United States Patent [19]

Ohashi et al.

[11] Patent Number: 4,990,516
[45] Date of Patent: Feb. 5, 1991

[54] AMELIORATING AGENT FOR DYSMNESIA

[75] Inventors: Mitsuo Ohashi; Fukutaro Taga; Takashi Hirayama, all of Saitama, Japan

[73] Assignee: Kyorin Seiyaku Kabushiki Kaisha, Tokyo, Japan

[21] Appl. No.: 434,409

[22] Filed: Nov. 13, 1989

[30] Foreign Application Priority Data

Nov. 11, 1988 [JP] Japan .................. 63-285217

[51] Int. Cl.$^5$ .................................. A61K 31/44
[52] U.S. Cl. ................................... 514/299; 514/300
[58] Field of Search .................... 514/299, 300

[56] References Cited

PUBLICATIONS

Chem. Abst., 105-218685K (1986) & 110-23786Q (1989).

Primary Examiner—Stanley J. Friedman
Attorney, Agent, or Firm—McAulay, Fisher, Nissen & Goldberg

[57] ABSTRACT

An ameliorating agent for dysmnesia, comprising as an effective component or components at least one of pyrazolo[1,5-a]pyridine derivatives represented by the general formula:

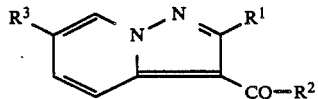

wherein $R^1$ and $R^2$ are independently hydrogen or a lower alkyl of 1–4 carbons, $R^3$ is hydrogen or a lower alkyl of 1–3 carbons or a lower alkoxy of 1–3 carbons.

1 Claim, No Drawings

AMELIORATING AGENT FOR DYSMNESIA

BACKGROUND OF THE INVENTION

1. Field of the Invention

The present invention relates to an ameliorating agent for dysmnesia (impairment of memory), particularly to an ameliorating agent for dysmnesia containing a derivative of pyrazolo[1,5-a]pyridine as an effective component.

2. Related Background Art

Recently diseases such as senile dementia accompanying dysmnesia have become a great medical and social problem as a result of elongation of human life.

Dysmnesia patients show a loss of intellectual ability, dysmnesia (namely, impairment of memory), impairment of abstract thinking, aphasia, apraxia, disorientation, etc. Such impairment of the fundamental function results from the disorder of formation of memory or of reproduction of the memory retained. However, no effective medicine therefor is said to be found at the moment, so that early development of the treating medicine is strongly desired.

The pyrazolo[1,5 a]pyridine derivatives represented by the general formula below found by Irikura et al. are known (Japanese Patent Publication No. 52-29318 corresponding to U.S. Pat. No. 3,850,941, U.K. Patent 1,378,375 and so on) to be effective for treatment of circulatory organ disease, prevention and treatment of bronchial asthma, antiallergic action for ophthalmic disease, and antirheumatic action, and still further be useful for treatment cerebrovascular disease:

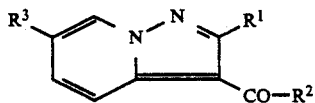

wherein $R^1$ and $R^2$ are independently hydrogen or a lower alkyl of 1–4 carbons, $R^3$ is hydrogen or a lower alkyl of 1–3 carbons or a lower alkoxy of 1–3 carbons.

Such pyrazolo[1,5-a]pyridine derivatives, however, are not known to have an action of ameliorating dysmnesia until now.

SUMMARY OF THE INVENTION

The inventors of the present invention have made comprehensive study seeking for an effective medicine for treatment of dysmnesia particularly among symptoms of dementia in view of the circumstance mentioned above, and have found that the pyrazolo[1,5 a]pyridine derivatives which are known to be effective for treatment of circulatory organ disease have a remarkable ameliorating effect for dysmnesia.

The object of the present invention is to provide an ameliorating agent for dysmnesia.

The present invention provides an ameliorating agent for dysmnesia, comprising as an effective component or components at least one of pyrazolo[1,5 a]pyridine derivatives represented by the general formula:

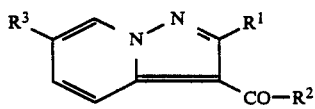

wherein $R^1$ and $R^2$ are independently hydrogen or a lower alkyl of 1–4 carbons, $R^3$ is hydrogen or a lower alkyl of 1–3 carbons or a lower alkoxy of 1–3 carbons.

DETAILED DESCRIPTION OF THE PREFERRED EMBODIMENTS

The effective component of the ameliorating agent for dysmnesia, namely pyrazolo[1,5-a]pyridine represented by the above general formula is specifically exemplified by 3-isobutyryl-2-isopropylpyrazolo[1,5-a]pyridine (m.p.: 53.5°–54° C.), 2-methyl-3-acetylpyrazolo[1,5-a]pyridine (m.p.: 86°—87° C.), 2-ethyl-3-propionylpyrazolo[1,5 a]pyridine (m.p.: 105.5°–106° C.), 2-isobutyl-3-isovalerylpyrazolo[1,5-a]pyridine (m.p. 53°–54° C.), 2,6-dimethyl-3-acetylpyrazolo[1,5-a]pyridine (m.p.: 141°–142° C.), 2-methyl-3-acetyl-6-methoxypyrazolo[1,5-a]pyridine (m.p.: 123° C.), 3-acetyl 2-isopropylpyrazolo[1,5-a]pyridine (m.p.: 74° C.), 3-acetyl-2-n-propylpyrazolo[1,5 a]pyridine (m.p.: 98°–99° C.), 3-formyl-2-isopropylpyrazolo[1,5 apyridine (m.p.: 81°–81.5° C.), 3-acetylpyrazolo[1,5 a]pyridine (m.p.: 96°–97° C.), and 3-isobutyryl-2-methylpyrazolo[1,5-a]pyridine (b.p.: 139°–145° C./5 mmHg).

The dysmnesia ameliorating agent of the present invention may be administered to a patient in a form for an oral medicine, a liniment medicine, or an injection medicine. Thus the form of the agent is exemplified by tablets, capsules, and granules for an oral medicine. Suppositories, ointments, and injections are also exemplified. The other ingredients for providing such various types of medicines include, for example, excipients such as starch, lactose, and hydroxypropylcellulose; binders such as hydroxypropylcellulose, and carboxymethylcellulose; lubricants such as magnesium stearate and starch for oral preparations. Color, taste or flavor may be added to oral preparations. Fatty base materials, such as cacao butter, Witepsol (tradename, made by Dynamite Nobel Co., Ltd.), etc., may be used for suppositories. For injections, conventional materials, such as solubilizers, e.g. polyoxyethylene hydrogenated castor oil; isotonicities, e.g. xylitol, and lactose; etc may be used.

The dysmnesia ameliorating agent of the present invention is administered to a patient in one or three divisional doses of 1–500 mg per day, preferably 1–200 mg per day, more preferably 1–100 mg per day of the effective component, namely a pyrazolo1,5-a pyridine derivatives, the dose being adjusted suitable in accordance with the symptom and the age of the patient.

The dysmnesia ameliorating agent of the present invention containing a pyrazolo[1,5 a]pyridine as an effective component exhibits excellent effect of ameliorating dysmnesia in comparison with known cerebrovascular disease treating agents or brain metabolism activation agents which do not exhibit sufficient dysmnesia amelioration.

The examples below are intended to illustrate specifically the present invention.

EXAMPLE 1

200 mg of 3-isobutyryl-2-isopropylpyrazolo[1,5-a]pyridine (hereinafter referred to as Compound A) was dissolved by heating in 200 ml of physiological saline containing 1 % of polyoxyethylene hydrogenated castor oil to prepare an injection preparation containing Compound A at a concentration of 0.1%.

Animal experiments were conducted by employing an amnesic models with the above injection preparation to confirm the dysmnesia ameliorating effect.

1. Experimental animals:

Male mice of ddY strain (5-6 weeks of age) were employed.

2. Apparatus:

Avoidance Experiment Box of a step-through type (made by Ohara Ika Sangyo K.K.) consisting of light (14×10×11 cm) and a dark (18×12.5×12 cm) chambers. The light chamber was illuminated with a 20-W fluorescent lamp from approximately 15 cm above the light chamber. The two chambers were separated by a guillotine door. Each chamber has a floor made of a grid of stainless steel, only a grid in the dark chamber being connected to an electric stimulating apparatus so as to give an electric shock to the limbs of the animal.

3. Acquisition trial:

A mouse was put into the light chamber. After 10 seconds therefrom, the guillotine door was opened to allow the mouse to enter the dark chamber. Immediately after the four limbs of the mouse entered the dark room, the guillotine door was closed. Two seconds later, an electric shock of AC 45-50 V was given to the mouse for one second, and then immediately the mouse was taken out from the dark room.

4. Retention trial:

After 24 hours from the acquisition trial, the mouse was again put into the light chamber, and the same process was repeated except that the electric shock was not given. The time elapsed from the opening of the guillotine door before the mouse entered the dark chamber (Latency) was measured to the maximum of 300 seconds.

5. Amnesia-inducing operation:

(1) Amnesia induction by an electroconvulsive shock:

Immediately after the acquisition trial, an electroconvulsive shock (AC 100-140 V, 0.5 seconds) was given to the mouse from the both ears.

(2) Amnesia induction by cycloheximide:

Thirty minutes before the acquisition trial, cycloheximide was injected subcutaneously at a dose of 120 mg/kg.

(3) Amnesia induction by carbon dioxide:

Immediately after the acquisition trial, the mouse was put into a container of approximately 300 ml capacity filled with pure carbon dioxide, and was exposed to the gas for 25 seconds.

6. Dosage of the test compounds:

The test compounds, nicardipine: a hydrochloride salt of methyl-2-[methyl(phenylmethyl)amino]ethyl ester of 1,4-dihydro-2,6-dimethyl-4-(3-nitrophenyl)-3,5-pyridinedicarboxylic acid; and physostigmine: a methyl carbamate ester of 1,2,3,3a,8,8a-hexahydro-1,3a,8-trimethylpyrrolo[2,3-b]indol-5-ol were dissolved in a physiological saline; aniracetam: 1-(4-methoxybenzoyl)-2-pyrrolidinone, and idebenone: 2-(10-hydroxydecyl)-5,6-dimethoxy-3-methyl-2,5-cyclohexadiene-1,4-dione were suspended in physiological saline containing 5% gum arabicum. The compound was injected intraperitoneally, immediately after the electroconvulsive shock in the test of amnesia induction by electric shock, or 30 minutes before the retention trial in the test of amnesia induction by cycloheximide or carbon dioxide.

7. Results:

The results of the experiments are shown in Table 1 to Table 3.

TABLE 1

Effect on Amnesia Induced by Electroconvulsive Shock

| Compound | Dose (mg/kg) | Number of animals | Latency (seconds) (mean ± S.E.) | Improvement (%) |
|---|---|---|---|---|
| No treatment | — | 50 | 288.5 ± 5.0 | |
| ECS treatment | — | 50 | 82.0 ± 10.2 | |
| Compound A | 5 | 27 | 146.9 ± 16.5* | 31.4 |
| | 10 | 30 | 160.5 ± 16.9** | 38.0 |
| | 20 | 30 | 174.1 ± 19.1** | 44.6 |
| No treatment | — | 30 | 300 ± 0 | |
| ECS treatment | — | 29 | 150.8 ± 2.7 | |
| Nicardipine | 5 | 30 | 118.9 ± 15.7 | −21.4 |
| | 10 | 30 | 141.8 ± 16.0 | −6.0 |
| No treatment | — | 30 | 300 ± 0 | |
| ECS treatment | — | 30 | 150.8 ± 2.7 | |
| Idebenone | 10 | 30 | 128.0 ± 19.0 | −15.3 |
| | 30 | 20 | 132.6 ± 21.8 | −12.1 |
| No treatment | — | 30 | 287.4 ± 7.1 | |
| ECS treatment | — | 30 | 73.3 ± 12.6 | |
| Aniracetam | 40 | 10 | 28.4 ± 5.1 | −20.9 |
| | 80 | 10 | 105.6 ± 33.7 | 15.0 |
| | 160 | 10 | 39.7 ± 14.4 | −15.7 |
| No treatment | — | 30 | 294.7 ± 4.3 | |
| ECS treatment | — | 30 | 100.8 ± 13.0 | |
| Physostigmine | 0.25 | 30 | 154.6 ± 21.5* | 27.7 |

ECS: Electroconvulsive shock
*Significant in comparison with ECS treated group ($P < 0.05$).
**Significant in comparison with ECS treated group ($P < 0.01$).
Improvement (%) =
$$\frac{\text{Latency (Agent-treated)} - \text{Latency (ECS-treated)}}{\text{Latency (non-treated)} - \text{Latency (ECS-treated)}} \times 100$$

TABLE 2

Effect on Amnesia Induced by Cycloheximide

| Compound | Dose (mg/kg) | Number of animals | Latency (seconds) (mean ± S.E.) | Improvement (%) |
|---|---|---|---|---|
| No treatment | — | 50 | 243.2 ± 12.2 | |
| CHI treatment | — | 50 | 115.4 ± 14.6 | |
| Compound A | 5 | 30 | 122.8 ± 21.0 | 5.4 |
| | 10 | 30 | 149.1 ± 21.8 | 26.1 |
| | 20 | 30 | 196.4 ± 22.9* | 63.2 |
| No treatment | — | 30 | 236.7 ± 13.3 | |
| CHI treatment | — | 30 | 114.0 ± 17.6 | |
| Nicardipine | 5 | 30 | 161.0 ± 18.8 | 38.3 |
| | 10 | 30 | 105.7 ± 20.4 | −6.8 |
| No treatment | — | 70 | 245.9 ± 9.7 | |
| CHI treatment | — | 70 | 129.2 ± 12.6 | |
| Idebenone | 5 | 40 | 154.2 ± 19.1 | 21.4 |
| | 10 | 40 | 191.5 ± 17.9 | 53.4 |
| | 30 | 40 | 107.1 ± 17.9 | −18.9 |
| No treatment | — | 40 | 259.7 ± 13.1 | |
| CHI treatment | — | 40 | 120.1 ± 17.2 | |
| Aniracetam | 50 | 40 | 155.6 ± 16.8 | 25.4 |
| | 100 | 40 | 122.4 ± 17.1 | 1.6 |
| No treatment | — | 30 | 234.1 ± 16.5 | |
| CHI treatment | — | 30 | 114.2 ± 16.8 | |
| Physostigmine | 0.1 | 30 | 131.6 ± 18.7 | 14.5 |
| | 0.2 | 30 | 162.6 ± 21.8 | 40.4 |

CHI: cycloheximide
*Significant in comparison with CHI treated group ($P < 0.05$).
Improvement (%) =
$$\frac{\text{Latency (Agent-treated)} - \text{Latency (CHI-treated)}}{\text{Latency (non-treated)} - \text{Latency (CHI-treated)}} \times 100$$

TABLE 3

Effect on Amnesia Induced by Carbon Dioxide

| Compound | Dose (mg/kg) | Number of animals | Latency (seconds) (mean ± S.E.) | Improvement (%) |
|---|---|---|---|---|
| No treatment | — | 20 | 233.2 ± 18.0 | |
| $CO_2$ treatment | — | 20 | 109.1 ± 25.0 | |
| Compound A | 5 | 20 | 102.9 ± 20.6 | −5.0 |
| | 10 | 20 | 188.4 ± 25.2* | 63.9 |
| No treatment | — | 40 | 259.1 ± 10.1 | |
| $CO_2$ treatment | — | 40 | 99.7 ± 15.5 | |
| Nicardipine | 5 | 20 | 139.0 ± 26.9 | 24.6 |

TABLE 3-continued

| Effect on Amnesia Induced by Carbon Dioxide | | | | |
|---|---|---|---|---|
| Compound | Dose (mg/kg) | Number of animals | Latency (seconds) (mean ± S.E.) | Improvement (%) |
| | 10 | 20 | 147.2 ± 27.0 | 29.8 |
| No treatment | — | 60 | 257.6 ± 9.9 | |
| $CO_2$ treatment | — | 60 | 143.0 ± 14.6 | |
| Idebenone | 3 | 30 | 160.2 ± 21.3 | 15.0 |
| | 10 | 30 | 164.6 ± 21.4 | 18.8 |
| | 30 | 30 | 136.8 ± 22.8 | −5.4 |
| No treatment | — | 20 | 266.0 ± 13.9 | |
| $CO_2$ treatment | — | 20 | 115.4 ± 26.5 | |
| Aniracetam | 50 | 20 | 134.9 ± 27.0 | 12.9 |
| No treatment | — | 20 | 252.5 ± 15.0 | |
| $CO_2$ treatment | — | 20 | 84.0 ± 15.9 | |
| Aniracetam | 100 | 20 | 174.0 ± 28.9** | 53.4 |
| No treatment | — | 20 | 266.0 ± 13.9 | |
| $CO_2$ treatment | — | 20 | 115.4 ± 26.5 | |
| Physostigmine | 0.2 | 20 | 222.5 ± 24.9** | 71.1 |

*Significant in comparison with $CO_2$ treated group ($P < 0.05$).
**Significant in comparison with $CO_2$ treated group ($P < 0.01$).
Improvement (%) =
$$\frac{\text{Latency (Agent-treated)} - \text{Latency (CO}_2\text{-treated)}}{\text{Latency (non-treated)} - \text{Latency (CO}_2\text{-treated)}} \times 100$$

As shown in Tables, the compound of the present invention exhibits significant ameliorating effect on experimentally induced amnesia in comparison with a circulatory function ameliorating agent (nicardipine), a brain metabolism function activating agent (idebenone), an intellectualizing agent (aniracetam), and anticholinesterase agent (physostigmine).

EXAMPLE 2

20.0 g of Compound A was passed through a 100 mesh sieve, and then mixed with 350.0 g of lactose (150 mesh), 152.5 g of dried starch and 2.5 g of magnesium stearate, and the mixture was passed through a 50 mesh sieve.

After repetition of mixing and sieving, the mixture was filled in capsules in a conventional manner to prepare a capsule preparation containing 210 mg of the mixture (10 mg of Compound A) per capsule.

EXAMPLE 3

15.0 g of Compound A was passed through a 100 mesh sieve, and then mixed with 244.5 g of lactose (150 mesh), 112.5 g of dried starch and 3.0 g of magnesium stearate, and the mixture was passed through a 50 mesh sieve.

After repetition of mixing and sieving, the mixture was filled in capsules in a conventional manner to prepare a capsule preparation containing 250 mg of the mixture (10 mg of Compound A) per capsule.

EXAMPLE 4

30.0 g of Compound A was passed through a 100 mesh sieve, and then mixed with 229.5 g of lactose (150 mesh), 112.5 g of dried starch and 3.0 g of magnesium stearate, and the mixture was passed through a 50 mesh sieve.

After repetition of mixing and sieving, the mixture was filled in capsules in a conventional manner to prepare a capsule preparation containing 250 mg of the mixture (10 mg of Compound A) per capsule.

EXAMPLE 5

Into 24.96 kg of Witepsol W-35 heated to approximately 60° C. and melted, 194 g of Compound A was added and dissolved by stirring. It was cooled to approximately 37° C., and fractionally filled into plastic suppository containers in an amount of 1.3 g per container by means of an automatic suppository filling and packing machine (made by Ramp Co.). Subsequently, having been cooled to 20°–18° C., it was sealed and packaged to prepare a suppository containing 10 mg of Compound A per suppository piece.

We claim:

1. A method for treating dysmnesia in a patient comprising administering to the patient an antidymnesia effective amount of the composition comprising pyrazolo [1,5-a]pyridine derivatives having the formula:

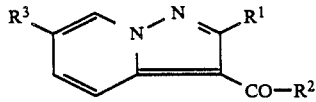

wherein $R^1$ and $R^2$ are independently hydrogen or a lower alkyl of 1-4 carbons, $R^3$ in hydrogen or a lower alkyl of 1-3 carbons or a lower alkoxy of 1-3 carbons, and a pharmaceutically acceptable carrier therefore.

* * * * *